United States Patent
Dutta et al.

(10) Patent No.: US 6,299,595 B1
(45) Date of Patent: Oct. 9, 2001

(54) CATHETERS HAVING RAPID-EXCHANGE AND OVER-THE-WIRE OPERATING MODES

(75) Inventors: Debashis Dutta, Santa Clara; Cindy Nguyen, San Jose; Eugene Serina, Menlo Park; Kristin E. Welborn, Santa Clara, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/466,365

(22) Filed: Dec. 17, 1999

(51) Int. Cl.$^7$ .................................................. A61M 29/00
(52) U.S. Cl. ........................................ 604/96; 604/103.04
(58) Field of Search .................................. 604/96, 97, 98, 604/100, 101, 102, 103.04, 534, 535, 284; 606/191–194

(56) References Cited

U.S. PATENT DOCUMENTS

| | | |
|---|---|---|
| 4,323,071 | 4/1982 | Simpson et al. . |
| 4,411,055 | 10/1983 | Simpson et al. . |
| 4,616,652 | 10/1986 | Simpson . |
| 4,661,094 | 4/1987 | Simpson . |
| 4,669,469 | 6/1987 | Gifford, III et al. . |
| 4,748,982 | 6/1988 | Horzewski et al. . |
| 4,762,129 | 8/1988 | Bonzel . |
| 4,771,777 | 9/1988 | Horzewski et al. . |
| 4,838,268 | 6/1989 | Keith et al. . |
| 4,943,278 | 7/1990 | Euteneuer et al. . |
| 5,015,231 | 5/1991 | Keith et al. . |
| 5,021,044 | 6/1991 | Sharkawy . |
| 5,040,548 | 8/1991 | Yock . |
| 5,061,273 | 10/1991 | Yock . |
| 5,087,394 | 2/1992 | Keith . |
| 5,141,494 | 8/1992 | Danforth et al. . |
| 5,147,302 | 9/1992 | Euteneuer et al. . |
| 5,156,594 | 10/1992 | Keith . |
| 5,192,295 | 3/1993 | Danforth et al. . |
| 5,195,978 | * 3/1993 | Schiffer .............................. 604/161 |
| 5,217,482 | 6/1993 | Keith . |
| 5,232,445 | 8/1993 | Bonzel . |
| 5,246,420 | 9/1993 | Kraus et al. . |
| 5,300,085 | 4/1994 | Yock . |
| 5,312,340 | 5/1994 | Keith . |
| 5,350,395 | 9/1994 | Yock . |
| 5,370,616 | 12/1994 | Keith et al. . |

(List continued on next page.)

*Primary Examiner*—Manuel Mendez
(74) *Attorney, Agent, or Firm*—Fulwider Patton Lee & Utecht, LLP

(57) ABSTRACT

An intravascular catheter capable of both rapid-exchange and over-the-wire modes of operation having a relatively long proximal shaft portion, a relatively short distal section and an intermediate shaft section, which connects the proximal shaft section and the distal shaft section. In one embodiment, the intermediate shaft section includes a guide wire port and a first guide wire lumen which extends throughout both the intermediate and distal shaft section, and a second guide wire lumen which extends throughout the entire catheter shaft. In another embodiment, the intermediate shaft section includes a y-lumen junction which allows a first guide wire lumen introduced at the intermediate shaft section and a second guide wire lumen extending from the proximal end of the catheter shaft throughout the proximal shaft section to merge and communicate with a single distal guide wire lumen which extends from the intermediate shaft section to the distal end of the catheter shaft. In another embodiment, the catheter shaft includes a single guide wire lumen extending from the proximal end to the distal end wherein the guide wire lumen is defined by a proximal section and a distal section. The proximal section guide wire lumen includes a slit which allows a guide wire to be removed for rapid-exchange mode of operation or retained for over-the-wire mode of operation.

2 Claims, 3 Drawing Sheets

U.S. PATENT DOCUMENTS

| | | |
|---|---|---|
| 5,387,225 | 2/1995 | Euteneuer et al. . |
| 5,395,332 | 3/1995 | Ressemann et al. . |
| 5,395,334 | 3/1995 | Keith et al. . |
| 5,447,497 | 9/1995 | Sogard et al. . |
| 5,451,233 | 9/1995 | Yock . |
| 5,496,346 | 3/1996 | Horzewski et al. . |
| 5,501,227 | 3/1996 | Yock . |
| 5,516,336 | 5/1996 | McInnes et al. . |
| 5,522,818 | 6/1996 | Keith et al. . |
| 5,567,203 | 10/1996 | Euteneuer et al. . |
| 5,571,087 | 11/1996 | Ressemann et al. . |
| 5,571,094 * | 11/1996 | Sirhan .................................. 604/284 |
| 5,578,009 | 11/1996 | Kraus et al. . |
| 5,645,533 | 7/1997 | Blaeser et al. . |
| 5,658,251 | 8/1997 | Ressemann et al. . |
| 5,702,364 | 12/1997 | Euteneuer et al. . |
| 5,702,439 | 12/1997 | Keith et al. . |
| 5,718,680 | 2/1998 | Kraus et al. . |
| 5,720,724 | 2/1998 | Ressemann et al. . |
| 5,769,868 | 6/1998 | Yock . |
| 5,807,355 * | 9/1998 | Ramzipoor et al. .................. 604/282 |
| 5,843,022 | 12/1998 | Willard et al. . |
| 5,865,178 | 2/1999 | Yock . |
| 5,902,245 | 5/1999 | Yock . |
| 5,921,958 | 7/1999 | Ressemann et al. . |
| 6,004,291 | 12/1999 | Ressemann et al. . |
| 6,036,715 | 3/2000 | Yock . |
| 6,099,497 * | 8/2000 | Adams et al. ..................... 604/96.01 |

* cited by examiner

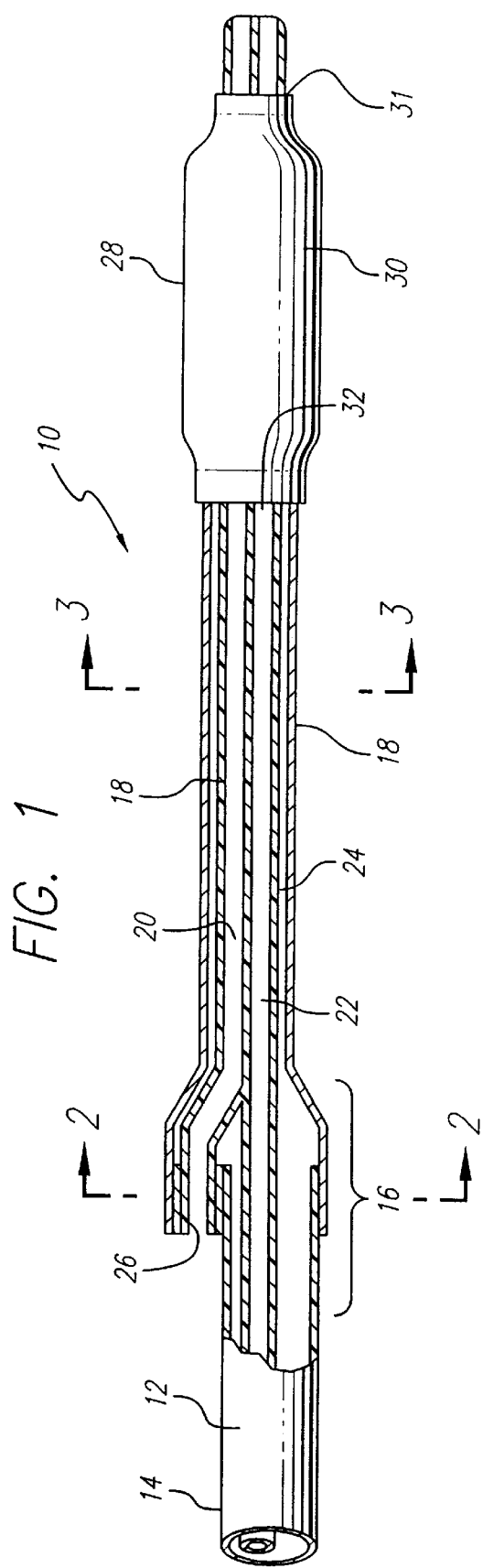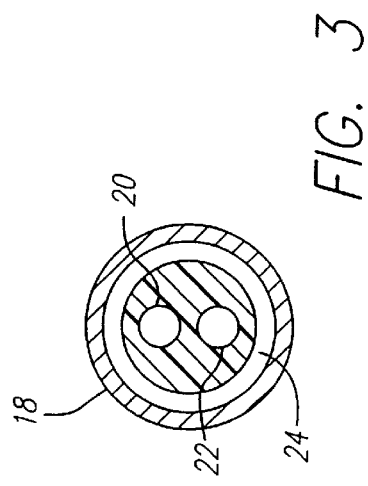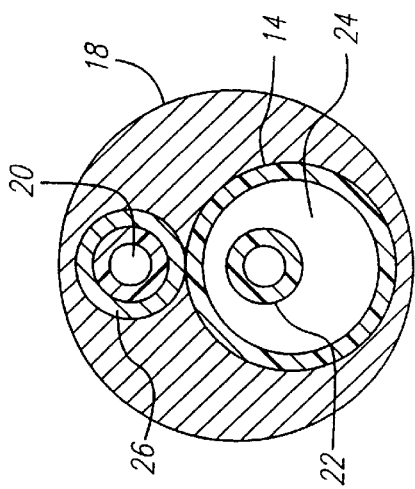

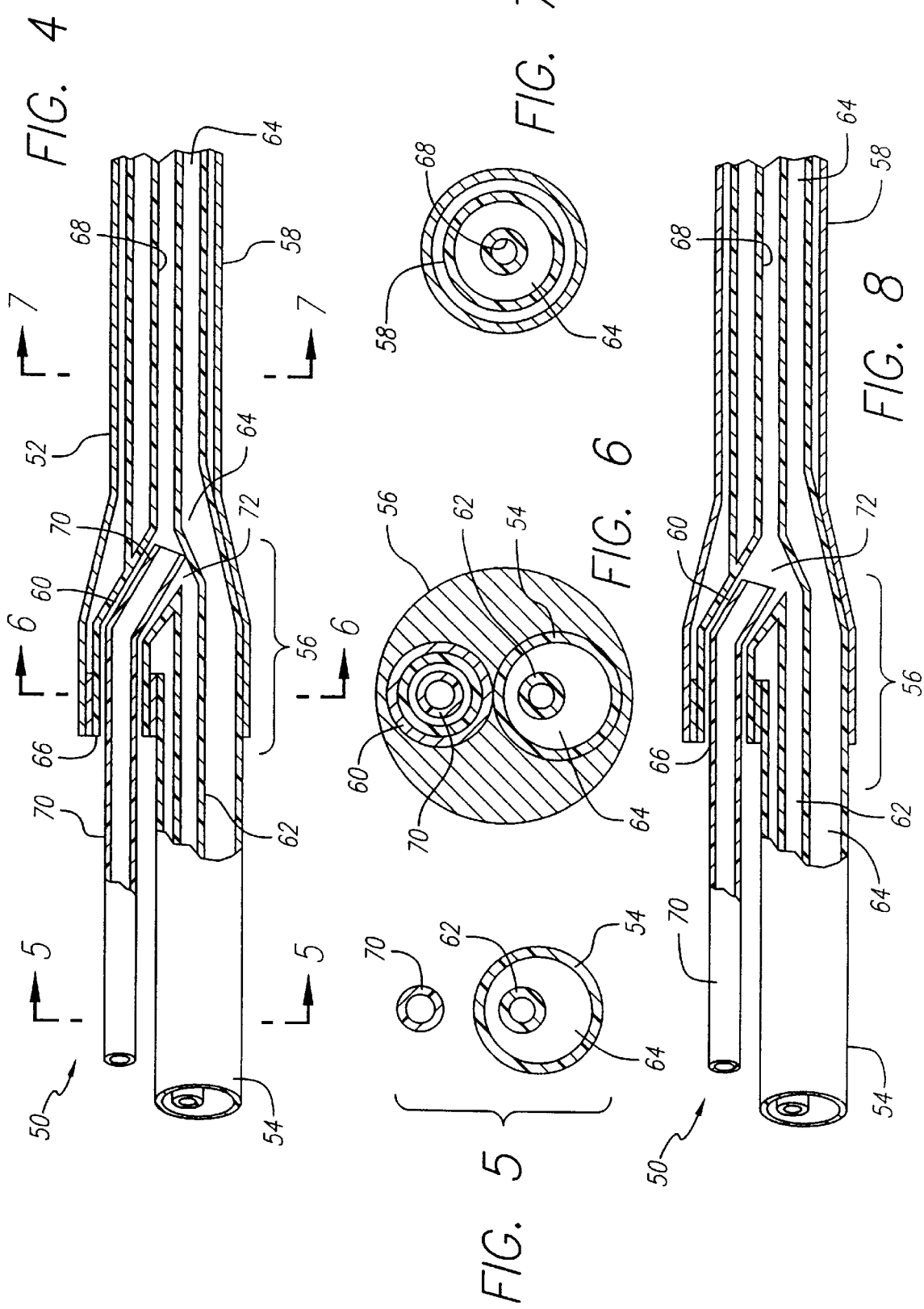

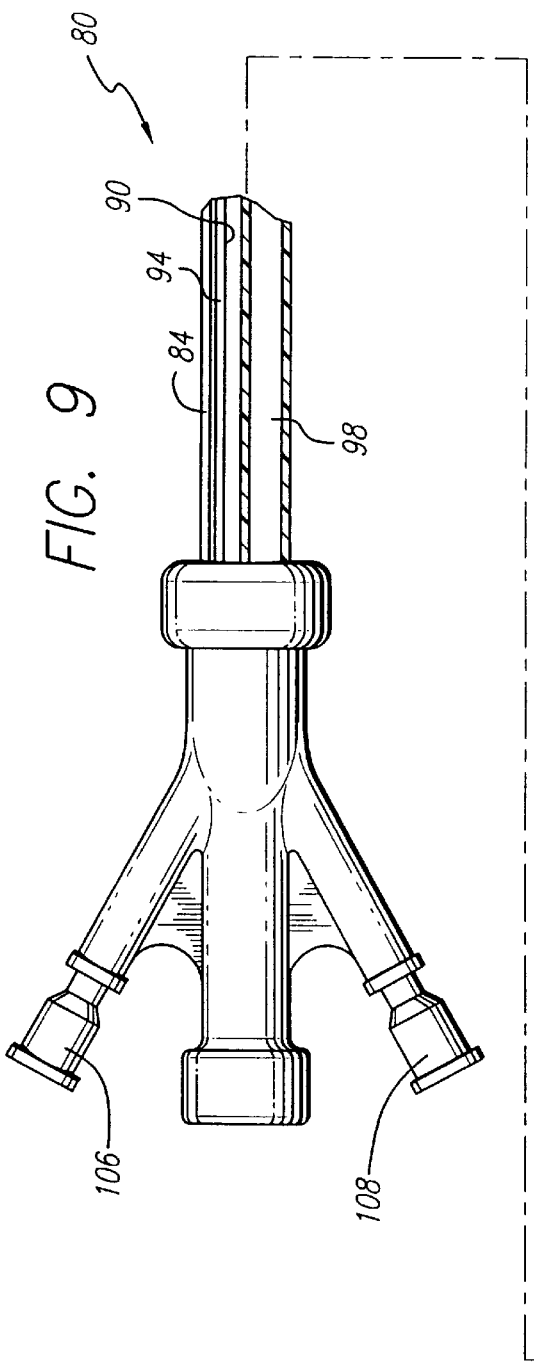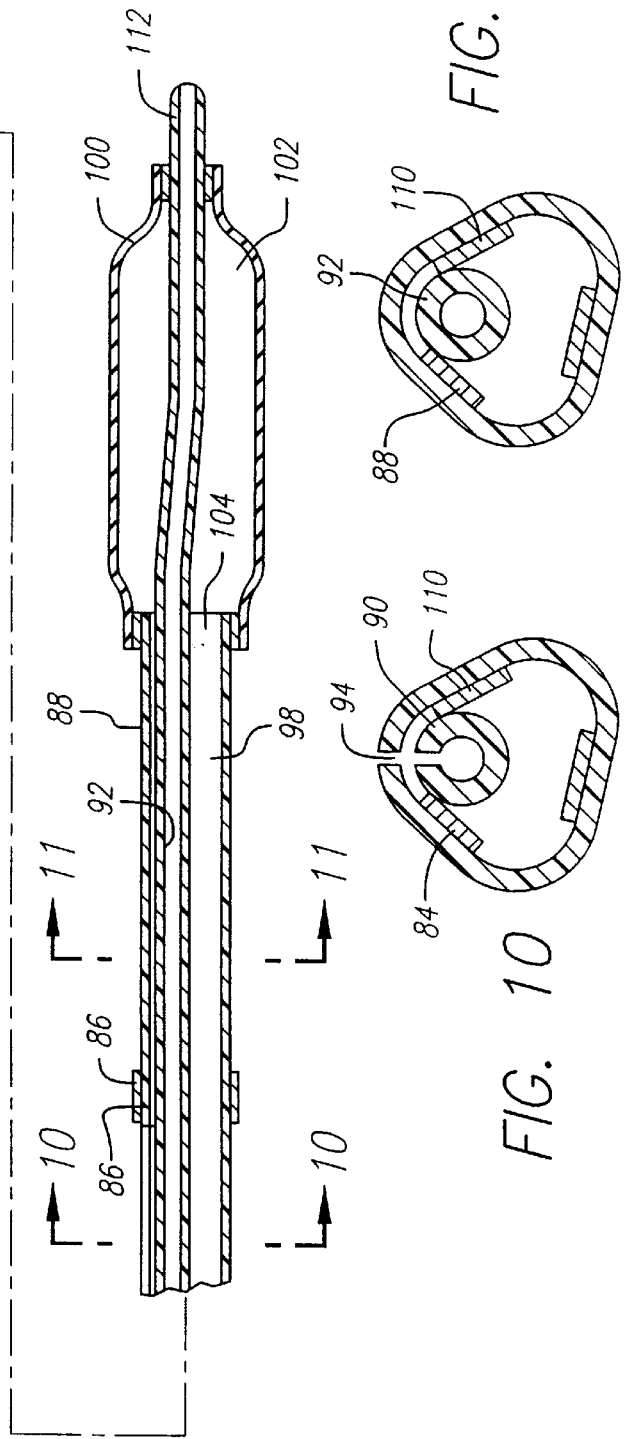

CATHETERS HAVING RAPID-EXCHANGE AND OVER-THE-WIRE OPERATING MODES

BACKGROUND OF THE INVENTION

The present invention generally relates to intravascular procedures, such as treating carotid arteries and percutaneous transluminal coronary angioplasty (PTCA), and particularly to an intravascular catheter which can be utilized in a rapid-exchange (RX) or over-the-wire (OTW) operating mode.

In typical PTCA procedures utilizing over-the-wire mode, a dilation catheter is advanced over a guide wire slidably disposed within an inner lumen of the dilation catheter into a patient's coronary artery until the balloon on the distal extremity of the dilation catheter is properly positioned across the lesion to be dilated. Once properly positioned across the lesion, the flexible, relatively inelastic dilatation balloon on the catheter is inflated to a predetermined size with radiopaque liquid at relatively high pressures (e.g., generally 4–20 atmospheres) to dilate the stenosed region of the diseased artery. One or more inflations of the balloon may be required to complete the dilation of the stenosis. After the last dilation, the balloon is deflated so that the dilatation catheter can be removed from the dilated stenosis and so that blood flow can resume through the dilated artery.

One significant improvement in dilatation catheters has been the introduction of rapid-exchange type dilatation catheters. These catheters have a short guide wire receiving sleeve or inner lumen extending through the distal portion of the catheter which extend from a distal guide wire port in the distal end of the catheter to a proximal guide wire port spaced proximal to the proximal end of the dilatation balloon. The proximal guide wire port is usually located at least about 10 cm. and usually not more than about 50 cm. from the distal guide wire port. A slit is preferably provided in the catheter wall which extends from the second guide wire port, preferably to a location proximal to the proximal end of the inflatable balloon to aid in the removal of the catheter from a guide wire upon withdrawal of the catheter from the patient. The structure of the catheter allows for the rapid exchange of the catheter without the need for the use of an exchange wire or adding a guide wire extension to the proximal end of the guide wire. The design of this catheter has been widely praised by the medical profession and has met with much commercial success in the market place because of its unique design. The RX type dilation catheters of the assignee for the present invention, Advanced Cardiovascular Systems, Inc., have had a significant impact in the market for rapid-exchange type dilation catheters. Such products include dilatation catheters sold under the tradenames—The Alpha, The Streak, and The Ellipse.

However, there is one significant inconvenience with the use of RX type dilatation catheter systems, namely, the inability to remove a guide wire already in place within a patient's vasculature during an angioplasty procedure without losing access to the vascular location. There has been no convenient way in which to withdraw an in-place guide wire and then advance a replacement guide wire without losing access to the location of the distal end of the RX type dilatation catheter the short guide wire receiving inner lumen in the distal extremity of a RX type dilatation catheter. These instances occur when there is a need to replace an in-place guide wire with another guide wire having a different structure, e.g., an intermediate or standard wire with a core wire which extends to the distal tip of the guide wire. The need to withdraw an in-place guide wire also occurs when the distal tip of the in-place guide wire needs to be reshaped.

U.S. Pat. No. 5,807,355 (Ramzipoor et al.), which has been assigned to the present assignee, Advanced Cardiovascular Systems, Inc., describes an intravascular catheter with both RX and OTW operative modes. The Ranizipoor et al. patent is incorporated herein by reference. While this catheter provides for RX and OTW modes of operation, which is by choice of the operating physician, only one mode may be used at a time thus limiting the effective usefulness of the device. Additionally, the Ramzipoor dual mode catheter does not provide for a smooth RX guide wire exit port for used during RX modes. During such use, the RX guide wire will deform during passage through the expanded helical coil guide wire port. The need still exists therefore for a catheter which allows for simultaneous dual mode operation and which provides for a smooth exit notch. The present invention satisfies these and other needs.

SUMMARY OF THE INVENTION

This invention is directed to an elongated intravascular catheter which can be utilized in a rapid-exchange (RX) and/or an over-the-wire (OTW) mode of operation to perform an intravascular procedure, and particularly to a balloon dilatation catheter which can be used within the coronary arteries of a human patient during an angioplasty procedure.

The intravascular catheter of the invention generally comprises an elongated shaft with proximal and distal ends, a port in the distal end, a first lumen extending through the catheter from the port in the catheter distal end to a location spaced proximal to the proximal end of the balloon, and a second lumen extending through the catheter from the proximal end to the port in the distal end of the catheter. The catheter shaft has an elongated proximal section, an intermediate section, a relatively short distal section and a balloon or other means to perform an intravascular procedure on the distal section.

In the RX mode, the intravascular catheter can be advanced over an in-place guide wire within the first guide wire lumen while holding onto the proximal extremity of the guide wire extending out of the patient, until the distal end of the catheter is disposed within a desired location of the patient's vascular system. The in-place guide wire is external of the catheter proximal to the opening in the intermediate shaft section of the catheter. In this manner, the in-place guide wire can be removed by pulling on the proximal extremity thereof which extends out the patient and a replacement guide wire can be introduced into the proximal end of the catheter shaft, advanced through the catheter shaft in the second guide wire lumen in the OTW mode and then out the port in the distal end of the catheter.

For coronary artery use, the opening in the intermediate shaft section is preferably spaced longitudinally at least 30 cm from the distal end of the catheter shaft to ensure that it remains within a guiding catheter when the distal shaft section extends out into the patient's coronary artery.

In one embodiment, the distal shaft section of the catheter includes dual guide wire lumens, a first guide wire lumen entering the RX guide wire port in the intermediate shaft section, extending throughout the intermediate shaft section, the distal shaft section and then out the opening in the distal end of the catheter, and a second guide wire lumen extending throughout the entire catheter from the proximal shaft section to the distal shaft section and then out the port in the distal end of the catheter. The first guide wire lumen slidably receives an RX guide wire and the second guide wire lumen slidably receives an OTW guide wire.

In another embodiment of the invention, a y-section inner member having a slidable insert jacket provides a first (RX) guide wire lumen and a second (OTW) guide wire lumen of the proximal shaft section to communicate, forming a notch junction in the intermediate shaft section, wherein a single lumen, the distal section guide wire lumen, is formed which extends throughout the distal shaft section of the catheter and then out the port in the distal end of the catheter. The slidable insert jacket allows the physician to dictate the mode of operation. For the RX mode, the slidable insert jacket is pushed forward blocking off the second guide wire lumen at the notch junction and allowing the first guide wire lumen to be in fluid communication with the distal section guide wire lumen of the distal shaft section. For the OTW mode, the slidable insert jacket is slightly pulled back thus allowing the second guide wire lumen to be in fluid communication with the distal section guide wire lumen of the distal shaft section. Therefore, by a simple pull or push of the slidable insert jacket, the physician may choose either RX or OTW modes of operation.

In yet another embodiment, the proximal shaft section of the catheter comprises a lumen having a "peel-away" slit. The peel-away proximal shaft section serves both OTW and RX modes of operation. The guide wire lumen of the proximal shaft section has a slit which allows for the guide wire to be "peeled-away" and removed from the guide wire lumen, wherein the slit width is slightly smaller than the guide wire diameter thereby allowing the guide wire to remain within the lumen during the OTW mode of operation. The guide wire lumen slit, because of the deformable character of the material used, allows for the guide wire to be "peeled-away" or pulled out of the guide wire lumen via the guide wire lumen slit, thus allowing the RX mode of operation. The guide wire lumen slit runs throughout the proximal shaft section and ends in a location proximal to the distal shaft section at the intermediate shaft section. The intermediate shaft section is reinforced with a peel-away strain relief which ensures that the guide wire lumen slit will not propagate distally into the distal shaft section of the catheter.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is an elevational view, partially in section, of one embodiment of the invention.

FIG. 2 is a transverse cross-sectional view of the embodiment shown in FIG. 1 taken along lines 2—2.

FIG. 3 is a transverse cross-sectional view of the embodiment shown in FIG. 1 taken along lines 3—3.

FIG. 4 is an elevational view, partially in section, of another embodiment of the invention.

FIG. 5 is a transverse cross-sectional view of the embodiment shown in FIG. 4 taken along lines 5—5.

FIG. 6 is a transverse cross-sectional view of the embodiment shown in FIG. 4 taken along lines 6—6.

FIG. 7 is a transverse cross-sectional view of the embodiment shown in FIG. 4 taken along lines 7—7.

FIG. 8 is an elevational view, partially in section, of the embodiment shown in FIG. 4, configured for use in over-the-wire mode in which the insert sleeve is slightly pulled back.

FIG. 9 is an elevational view, partially in section, of another embodiment of the invention.

FIG. 10 is a transverse cross-sectional view of the embodiment shown in FIG. 9 taken along lines 10—10 depicting the peel-away slit of the proximal shaft section.

FIG. 11 is a transverse cross-sectional view of the embodiment shown in FIG. 9 taken along lines 11—11.

DETAILED DESCRIPTION OF THE PREFERRED EMBODIMENTS

The present invention provides for treatment of diseased vessels and arteries by giving the physician the option to utilize either an OTW or RX mode operation using the same catheter. In keeping with the invention, reference is made to FIGS. 1–3 which depict one embodiment of the current dual guide wire lumen catheter invention. In particular, the catheter 10 includes an elongated catheter shaft 12 with a relatively long proximal shaft section 14, an intermediate shaft section 16, and a relatively short distal shaft section 18. The catheter shaft 12 has a first guide wire lumen 20 which begins at the RX guide wire port 26 located near the distal end of the intermediate shaft section 16 and extends throughout the distal shaft section 18 and then out the distal end guide wire port 34 in the distal end of the catheter 10. The catheter also includes a second guide wire lumen 22 which extends throughout the catheter shaft 12 from the proximal end (not shown) of the proximal shaft section 14 to the distal end of the distal shaft section 18 and then out the distal end guide wire port 34. An inflation lumen 24 extends throughout the catheter shaft 12 from the proximal end of the proximal shaft section 14 to balloon opening 32 located at one end of the distal shaft section 18. A guide wire port 34 is provided in the distal end of the distal shaft section 18 which is in fluid communication with the first guide wire lumen 20 and the second guide wire lumen 22. Both the first guide wire lumen 20 and the second guide wire lumen 22 are capable of slidably receiving a guide wire. The distal shaft section 18 is further provided with a dilatation balloon 28 which has an interior 30 in fluid communication with the inflation lumen 24 through balloon opening 32.

As seen in FIG. 1, the proximal shaft section 14 and the distal shaft section 18 are interconnected at the intermediate shaft section 16. The proximal shaft section 14 is coupled to the distal shaft section by any means of adhesion, including laser bonding or fusion, glueing or melting. The communication between the proximal shaft section 14 and the distal shaft section 18 is provided by RX guide wire port 26. Additionally, the distal shaft section is in fluid communication with a dilatation balloon 28, the proximal end of the balloon is in communication with the distal shaft section via the balloon opening 32 and the distal end 31 of the balloon is attached to the distal end of the distal shaft section 18.

FIG. 2 depicts a cross-sectional view of the intermediate shaft section 16 of FIG. 1 taken along lines 2—2 wherein the intermediate shaft section encompasses the first guide wire lumen 20 and the proximal shaft section 14, which encompasses the second guide wire lumen 22 and the inflation lumen 24. FIG. 3 illustrates a cross-sectional view of the distal shaft section 18 which encompasses the first guide wire lumen 20, the second guide wire lumen 22 and the inflation lumen 24.

FIGS. 4 through 8 depict a preferred embodiment of the current invention. In particular, FIG. 4 depicts a notch junction catheter having an elongated catheter shaft 52 with a relatively long proximal shaft section 54, an intermediate shaft section 56, and a relatively short distal section 58. The catheter shaft 52 has a first guide wire lumen 60 which begins at the RX guide wire port 66, located near the proximal end of the intermediate shaft section 56, and which extends throughout the intermediate shaft section 56. The first guide wire lumen communicates with the distal section lumen 68 at the lumen y-junction 72. A second guide wire lumen 62, which begins at the proximal end of the proximal shaft section 54, extends throughout the proximal shaft section 54 and the intermediate shaft section 56 and communicates with the distal section lumen 68 at the lumen y-junction 72. A distal section lumen is in fluid communication with the first guide wire lumen 60 and the second guide wire lumen 62 at the lumen y-junction 72. The distal section lumen 68 extends from the lumen y-junction 72 throughout the distal shaft section 58 to the distal end of the catheter shaft 52.

As seen in FIG. 4, insert jacket 70 is used to determine the mode of operation, either the RX or OTW models. During use, insert jacket 70 is inserted into the RX guide wire port. For the RX mode of operation, the insert jacket is pushed distally into the first guide wire lumen until there is closed communication with the distal section guide wire lumen 68, thus allowing a guide wire to be slidably received by the distal section guide wire lumen 68 through the insert jacket 70 placed within the first guide wire lumen 60. As depicted in FIG. 8, for the OTW mode of operation, the insert jacket is pulled proximally or placed slightly proximal to the distal section guide wire lumen 68 within the first guide wire lumen 60, thereby allowing the second guide wire lumen 62 to be in fluid communication with the distal section guide wire lumen 68. This fluid communication between the second guide wire lumen 62 and the distal section guide wire lumen 68 allows for a guide wire to extend throughout the catheter shaft 52 in the OTW mode of operation.

For further clarification, FIGS. 5–7 depict cross-sectional views taken at various locations along the catheter shaft 52. FIG. 5 depicts a cross-sectional view of the proximal shaft section 54 of FIG. 4 taken along lines 5—5 wherein the proximal shaft section 54 encompasses the second guide wire lumen 62 and the inflation lumen 64. The insert jacket 70 is located externally of the proximal guide wire lumen. FIG. 6 depicts a cross-sectional view of the intermediate shaft section 56 of FIG. 4 taken along lines 6—6 wherein the intermediate shaft section 56 encompasses the first guide wire lumen 60 which further encompasses the insert jacket 70 and the proximal shaft section 54, which encompasses the second guide wire lumen 62 and the inflation lumen 64. FIG. 7 depicts a cross-sectional view of the distal shaft section 58 of FIG. 4 taken along lines 7—7 wherein the distal shaft section 58 encompasses the distal section guide wire lumen 68 and the inflation lumen 64.

FIGS. 9–11 illustrate yet another embodiment of the invention. In particular, FIG. 9 depicts the peel-away catheter having an elongated catheter shaft 82 with a relatively long proximal shaft section 84, an intermediate shaft section 86, and a relatively short distal section 88. The catheter shaft 82 has a guide wire lumen comprised of the proximal section guide wire lumen 90 and distal section guide wire lumen 92, an inflation lumen 98, a balloon 100 located in the distal shaft section 88, and an optional support mandrel 110 providing support for the catheter shaft 82. The proximal shaft section comprises an inflation lumen 98, a proximal section guide wire lumen 90 and a guide wire lumen slit 94. The guide wire lumen slit 94 is aligned parallel to and along the length of the proximal shaft section 84 and provides the peel-away mechanism of the proximal shaft section 84. The guide wire lumen slit 94 is smaller in width than the diameter of the typical guide wire, therefore during use, the guide wire is retained within the proximal section guide wire lumen unless force is exerted by the physician to pull the guide wire out of the guide wire lumen slit 94 and peel it away from the catheter.

The intermediate shaft section 86 includes the proximal section guide wire lumen 90 wherein the proximal section guide wire lumen 90 comes into fluid contact with the distal section guide wire lumen 92, the inflation lumen 98, and the peel-away strain relief 96. The peel-away strain relief 96 is positioned on the outside circumference of the intermediate shaft section 86 and provides resistance from the propagation of the guide wire lumen slit 94 of the proximal shaft section 84 into the distal shaft section 88. The peel-away strain relief may be constructed of the same material as the catheter shaft.

The distal shaft section 88 includes the inflation lumen 98, the balloon 100 and the distal section guide wire lumen 92. The distal section guide wire lumen 92 is in continuous contact and in fluid communication with the proximal section guide wire lumen 90 at the intermediate shaft section 86 as described above. The balloon is located at the distal end of the distal shaft section and is defined by a proximal end, distal end, and an interior. The proximal end of the balloon 100 is in fluid communication with the inflation lumen 98 via the balloon opening 104, the distal end of the balloon defines the end of the catheter shaft and ends at the distal end guide wire port 112. The proximal end of the balloon 100 is permanently connected to the distal shaft section 88 at a location slightly proximal to the end of the catheter shaft 82.

For further clarification, FIGS. 10 and 11 depict cross-sectional views taken at various locations along the catheter shaft 82. FIG. 10 depicts a cross-sectional view of the proximal shaft section 84 of FIG. 9 taken along lines 10—10 wherein the proximal shaft section 54 encompasses the proximal section guide wire lumen 90 and the inflation lumen 98. The guide wire lumen slit 94 allows for an opening in the proximal section guide wire lumen 90, however, because the guide wire lumen slit 94 typically is closed or at least defines a very narrow gap that is smaller than the diameter of the typical guide wire to be used with this catheter, the guide wire is retained within the proximal section guide wire lumen 90 unless force is exerted by the operating physician to pull the guide wire out of the guide wire lumen slit 94. FIG. 11 depicts a cross-sectional view of the distal shaft section 88 of FIG. 9 taken along lines 11—11 wherein the distal shaft section 88 encompasses the distal section guide wire lumen 92 and the inflation lumen 98. Both FIGS. 10 and 11 illustrate the optional support mandrel which adds stiffness to the catheter shaft which allows for easier handling of the catheter during introduction into the patient's vasculature.

From FIG. 9 it is seen that for the RX mode of operation, the guide wire is inserted in the proximal end of the proximal shaft section 84 and into the proximal section guide wire lumen 90. The guide wire traverses the length of the proximal section guide wire lumen 90 into the distal section guide wire lumen 92 and out the distal end guide wire port 112. After the catheter is in place in the patient's vasculature, the guide wire lumen slit 94 in the proximal shaft section guide wire lumen 90 allows for the guide wire to be quickly removed by pulling it out of the guide wire lumen slit. Furthermore, as seen from FIG. 9, for the OTW mode of operation, the guide wire is inserted in the proximal end of the proximal shaft section 84 into the proximal section guide wire lumen 90. The guide wire traverses the length of the proximal section guide wire lumen 90 into the distal section guide wire lumen 92 and out the distal end guide wire port 112. After the catheter is in place in the patient's vasculature, the guide wire remains in the proximal section guide wire lumen 90 and may be removed by pulling it out of the catheter shaft by the operating physician, at the proximal end of the proximal shaft section 84.

The use of the catheters of the invention for the most part follow the procedures described in U.S. Pat. No. 5,135,535 (Kramer), assigned to the present assignee (Advanced Cardiovascular Systems, Inc.). The Kramer patent is incorporated herein by reference.

The catheter shaft of the invention can be formed by conventional techniques well known in the art, e.g., extruding from a variety of polymer materials already found useful in intravascular catheters such as polyethylene, polyimide, polyamide, PVC, polyester (e.g., Hytrel) and high strength polymers such as polyetheretherketone (PEEK). The various components of the catheter can be joined by conventional adhesives, such as acrylonitrile based adhesives, heat shrinking, fusion bonding and the like.

The traverse dimensions of the catheter shaft and the guide wire lumens are for the most part determined by the transverse dimensions of the guide wire to be used in the catheter. Typically, the guide wire is about 0.008 to about 0.035 inch (0.2–0.9 mm) in diameter. The guide wire lumen is configured to slidably receive the guide wire, i.e., it should be about 0.001 to about 0.005 inch (0.025–0.13 mm) larger than the guide wire diameter. The catheter shaft is sufficiently long to extend from outside the proximal end of the guiding catheter, which likewise extends out of the patient during the procedure, to a vascular location where the procedure is to be performed. Typically, the catheter is about 135 cm in length. In the peel-away catheter embodiment, the guide wire lumen slit 94 should have a width smaller than that of the guide wire diameter in order to retain the guide wire within the proximal section guide wire lumen 90 for the OTW mode of operation. Additionally the slit width should be sufficiently wide enough to allow deformation when force is applied by the operating physician in order to pull the guide wire out of the proximal section guide wire lumen via the guide wire lumen slit for the RX mode of operation.

While the invention is described herein in terms of a dilatation catheter, those skilled in the art will recognize that it is applicable to a variety of intravascular catheters. Additionally, while several particular forms of the invention have been illustrated and described, it will be apparent that to those skilled in the art that various modifications can be make without departing from the spirit and scope of the invention. Although individual features of embodiments of the invention may be shown in some of the drawings and not in others, those skilled in the art will recognize that individual features of one embodiment of the invention can be combined with any or all the features of another embodiment.

What is claimed:

1. An intravascular catheter, comprising:

an elongated shaft defined by a proximal section, an intermediate section and a distal section wherein said proximal shaft section is attached to said distal section at said intermediate section;

a first guide wire port in said intermediate section;

a first guide wire lumen extending therein from said first guide wire port;

a second guide wire port at the proximal end of said proximal section;

a second guide wire lumen extending from said second guide wire port throughout said proximal and intermediate shaft sections;

a distal section guide wire lumen extending from said intermediate shaft section to the distal end of said distal shaft section;

a lumen y-junction in said intermediate shaft section through which said first guide wire lumen communicates with said distal section guide wire lumen and said second guide wire lumen may be selected to communicate with said distal section guide wire lumen;

a balloon attached to said distal shaft section for performing an intravascular procedure; and an inflation lumen extending from said proximal end of said proximal shaft section to the proximal end of said balloon at a balloon opening and in fluid communication with said balloon at said balloon opening.

2. The intravascular catheter of claim 1, further comprising longitudinally shiftable insert jacket positioned within the first guide wire lumen via the first guide wire port whereby the communication between said second guide wire lumen and said distal section guide wire lumen may be selected such that an operating physician can choose either a rapid-exchange or an over-the-wire mode of operation.

* * * * *

UNITED STATES PATENT AND TRADEMARK OFFICE
CERTIFICATE OF CORRECTION

PATENT NO. : 6,299,595 B1
DATED : October 9, 2001
INVENTOR(S) : Debashis Dutta et al.

It is certified that error appears in the above-identified patent and that said Letters Patent is hereby corrected as shown below:

<u>Column 8, claim 2,</u>
Line 40, after "ing", add -- a --.

Signed and Sealed this

Twenty-sixth Day of March, 2002

*Attest:*

JAMES E. ROGAN
*Attesting Officer*   *Director of the United States Patent and Trademark Office*